United States Patent [19]

Shorr et al.

[11] Patent Number: 5,728,560
[45] Date of Patent: Mar. 17, 1998

[54] METHOD OF TREATING CD4+ T CELL LYMPHOPENIA IN IMMUNO-COMPROMISED PATIENTS

[75] Inventors: Robert G. L. Shorr, Edison, N.J.; Mike A. Clark, Big Pine Key, Fla.; David H. Goddard, Great Neck, N.Y.

[73] Assignee: Enzon, Inc., Piscataway, N.J.

[21] Appl. No.: 663,685

[22] Filed: Jun. 14, 1996

Related U.S. Application Data

[60] Provisional application No. 60/000,267 Jun. 16, 1995, No. 60/012,552 Feb. 29, 1996 and No. 60/015,365 Apr. 12, 1996.

[51] Int. Cl.$^6$ .......................... A61K 38/43; C12N 9/00; C12N 9/78
[52] U.S. Cl. .................. 435/183; 435/188; 435/227; 514/4; 514/21; 514/46
[58] Field of Search .................. 514/4, 21, 46; 435/188.5, 188, 227, 103; 424/175.1, 810

[56] References Cited

U.S. PATENT DOCUMENTS

| | | |
|---|---|---|
| 4,855,304 | 8/1989 | Devash . |
| 4,861,759 | 8/1989 | Mitsuya et al. . |
| 4,963,662 | 10/1990 | Matthes et al. . |
| 4,981,857 | 1/1991 | Daluge et al. . |
| 5,015,647 | 5/1991 | Daluge et al. . |
| 5,017,577 | 5/1991 | Daluge et al. . |
| 5,153,180 | 10/1992 | Matthes et al. . |
| 5,254,539 | 10/1993 | Mitsuya et al. . |
| 5,330,972 | 7/1994 | Cope . |

FOREIGN PATENT DOCUMENTS

WO 95/12618  5/1995  WIPO .

OTHER PUBLICATIONS

Burnham, N. Am J. Hosp Pharm 51:210 1994.
Jondal, M. et al., "Killing of immature CD+4CD8+ thymocytes in vivo by anti-CD3 or 5'-(N-ethyl)-carboxido Adenosine is blocked by clucocorticoid receptor antagonist RU-486*", Eur. J. Immunol., 1993. 23:1246-1250.
Xiang Gao et al., "Activation of Apoptosis in Early Mouse Embryos by 2"-Deoxyadenosine Exposure", Teratology, 1994, 49: 1-12.
Szondy, Z., "Adenosine stimulates DNA fragmentation in human thymocytes by Ca2+-mediated mechanisms" Biochem Journal, 1994., 304: 877-885.
Tanaka, Y. et al., "Apoptosis Induced by Adenisone in Human Leukemia HL-60 Cells", Experimental Cell Research, 1994, 213: 242-252.
Mangi, R. et al., "Depression of Cell-Mediated Immunity During Acute Infectious Mononucleosis", N Eng. J. Med. 291:1149-1153, 1974.

Casoli, C., et al., "Prognostic Significance of Adenoisine Deaminase Determinations In Subjects With the Lymphoadenopathy Syndrome", Jour. Med. Virology 24:413-422 (1988).
Martinez-Hernandez, D. et al., "Adenosine Deaminase in the Acquired Immunodeficiency Syndrome", Clinical Chemistry, vol. 34, No. 9, 1988.
Yoshitatsu, S. et al., "Evaluation of the effects of erythro-9(2-hydroxy-3-nonyl)) adenine (EHNA) on HIV-1 production in vitro", Biochem. and Biophys. Research Comm., vol. 164 #1, pp. 345-359, 1989.
Christensen L., et al., "Decreased B lymphocyte ecto-5'nucleotidase & increased adenosine deaminase in monomuclear cells from patients infected with human immunodeficiency virus", APMIS 96: 882-888, 1988.
Valls, V., et al., "Significance of adenosine deaminase measurement in sera of patients with HIV-1 infection", AIDS 1990, 4:465-373.
Niedzwicki, J., et al., "Plasma Adenosine Deaminase2: A Marker for Human Immuno-deficiency Virus Infection", Jour. of Acq. Immune Deficiency Syndrome 4:188-182, 1991.
Gougeon, M., et al., "Apoptosis in AIDS", Science, vol. 260 pp. 1269-1270, May 28, 1993.
Weiss, R., "How Does HIV Cause AIDS", Science, vol. 260, pp. 1273-1279, May 28, 1993.
Johnston, M., et al., "Present Status and Future Prospects for HIV Therapies", Science, vol. 260, pp. 1286-1293, May 28, 1993.
Palumbo, E., "Zidovudine treatment increases erythrocyte deaminase activity", AIDS 1991, vol. 5, No. 5, pp. 603-604.
Barchi, J., et al., "Potential Anti-AIDS Drugs. Lipophilic, Adenosine Deaminase-Activated Pro-Drugs."J. Med Chem., 1991, 34, 1647-1655.
Blaese, R., et al., "Gene Therapy for Primary Immunodeficiency Disease", Immunodeficiency Reviews 1992, vol. 3, pp. 329-341.

(List continued on next page.)

*Primary Examiner*—Thomas M. Cunningham
*Assistant Examiner*—Martha T. Lubet
*Attorney, Agent, or Firm*—Roberts & Mercanti, LLP

[57] ABSTRACT

The present invention is directed to methods of treating CD4+ T cell lymphopenia in HIV-infected patients. The methods include administering an effective mount of adenosine deaminase or related enzymatic material to a patient in need thereof. In preferred aspects of the invention, the method is employed in conjunction with HIV-infected patients having CD4+ T cell levels of less than about 200/µl. Effective amounts of the enzyme range from about 5 to about 50 IU/kg/week. In one particularly preferred aspect of the invention, the adenosine deaminase is conjugated to one or more strands of polyethylene glycol to prolonged activity in vivo.

18 Claims, No Drawings

OTHER PUBLICATIONS

Renouf, J., "Depressed Activities of Purine Enzymes of Lymphocytes of Patients Infected with Human Immunodeficiency Virus", Clinical Chemistry, vol. 35, No. 7, pp. 1478–1481, 1989.

Hirschhorn, R., "Overview of Biochemical Abnormalities and Molecular Genetics of Adenosine Deaminase Deficiency", Pediatric Research, vol. 33 (Supp.), No. 1, pp. S35–S41, 1993.

Marasco, W., et al., "Design, intracellular expression, and activity of a human anti-human immuno-deficiency virus type 1 gp120 single-chain antibody", Proc. Natl. Acad. Sci. USA, vol. 90, pp. 7889–7893, Aug. 1993, Medical Sciences.

Buonocore, L., et al., "Blockade of human imunodeficiency virus type 1 production in CD4+T cells by an intracellular CD4+ expressed under control of the viral long terminal repeat", Proc. Natl. A vol. 90, pp. 2695–2699, Apr. 1993, Medical Sciences.

Chelucci, C., et al., "In Vitro Human Immunodeficiency Virus-1 Infection of Purified Hematopoietic Progenitors in Single-Cell Culture", Blood, vol. 85, No. 5, Mar. 1, 1995, pp. 1181–1187.

Muro–Cacho, C., "Analysis of Apoptosis in Lymph Nodes of H IV–Infected Persons", Journal of Immunology, 1995, 154: 5555–5566.

Fairbanks, L. et al., "Adenosine Deaminase (ADA) Deficiency As The Unexpected Cause of CD4+ T–Lymphocytopenia in Two HIV–Neg. Adult Female . . . ", Adv. in Ex. Med. &Bio. V.370, pp. 471–474 (1994).

Blaese, R.M. et al., "Gene Therapy for Primary Immunodeficiency Disease", Immunodeficiency Reviews, vol. 3, pp. 329–349 (1992).

Vieria, J. et al., "PEG Adenosine Deaminase as a Therapuetic Adjuvant in the Treatment of Human Acquired Immunodeficiency Syndrome (AIDS)", Ab.#755, FASEB Jour., vol. 10, #3, Mar. 8, 1996.

Kim, I. K. et al., "Induction of Apoptosis and c–myc in L1210 Lymphocytic Leukemia Cells by Adenosine", J. of Biomed. Sci., vol. 1, #3, pp. 154–157, 1994.

METHOD OF TREATING CD4+ T CELL LYMPHOPENIA IN IMMUNO-COMPROMISED PATIENTS

CROSS-REFERENCE TO RELATED APPLICATIONS

This application claims the benefit of priority from the following provisional applications: application Ser. No. 60/000,267 filed Jun. 16, 1995 now abandoned, application Ser. No. 60/012,552 fled Feb. 29, 1996 now abandoned and application Ser. No. 60/015,365 filed Apr. 12, 1996. The contents of each of these applications are incorporated herein by reference.

BACKGROUND OF THE INVENTION

The present invention relates to methods of increasing CD4+ T cells in patients infected with the human immunodeficiency virus (HIV). In particular, the present invention relates to a novel use of adenosine deaminase for treating CD4+ T cell lymphopenia.

Acquired immunodeficiency syndrome (AIDS) is a disease characterized by a progressive loss of function of the immune system. As a result, those afflicted with the syndrome are susceptible to a variety of opportunistic infections. The etiologic agent of AIDS is a cytopathic retrovirus designated the human immunodeficiency virus (HIV). One of the major targets of the HIV in humans is T helper cells (CD4+ cells). The infection of T helper cells by HIV results in a profound dysregulation of the immune system including both depleted numbers and impaired functioning of T lymphocytes. Although the exact mechanism is unknown, the number of T helper cells predictably declines during HIV infection. Clinicians monitor this decline as an indicator of disease progression.

Research in the AIDS field has focused on several goals: preventing HIV infections, treating HIV-infected individuals with anti-viral agents, treating opportunistic infections with antimicrobial agents, and restoring the immune system of infected patients.

HIV gains entry into T helper cells by binding to receptors on the cell surface. Initial contact between the virus and the T cell is believed to occur by interaction of the external vital glycoprotein gp120 and the CD4 protein present on the surface of the T cell. Recently, it has been postulated that a second receptor on the T cells, the CD26 receptor may also be involved with facilitating HIV entry into T cells. CD26 also binds adenosine deaminase (ADA) on the surface of T lymphocytes and may play a role in T cell activation.

In HIV infection, the immune system is chronically activated. This chronic activation is believed to play a primary role in the pathology of the disease. The persistence of the virus and viral replication are thought to play a primary role in maintaining this state of immune activation. Evidence of this phenomenon includes spontaneous lymphocyte proliferation, activation of monocytes, expression of T cell activation antigens on the surface of T helper cells, increased cytokine expression and elevated levels of ADA in the serum and erythrocytes. Thus, the increase in ADA may be a consequence of activation of the immune system in response to infection. In view of this observation, there have been suggestions that plasma ADA and/or the isoenzyme ADA2 would be useful markers of the disease's progress. See AIDS 1990 4:365–373 and *J. of Acquired Immun. Defic. Synd.* 4:178–82 (1991). Alternatively, it has also been postulated that increase in ADA in HIV disease is an adaptive response by the immune system to decreasing numbers of T lymphocytes.

In contrast, Renouf et al. (*Clin. Chem.* 35:1478–1481, 1989) report that lymphocyte ADA levels are reduced in patients with HIV infection compared to uninfected controls. Nonetheless, in HIV-infected patients, the loss of CD4+ cells is associated with lymphocyte activation which does not result in cell proliferation as one would normally expect. Instead, this activation results in cell death by apoptosis which is also known as programmed cell death. This physiological suicide mechanism usually functions as a part of homeostasis i.e. normal tissue turnover. Apoptosis is essential in the normal maturation of the immune system. Apoptic cell death is part of the normal development of self-tolerance. Apoptosis, however, can be triggered in immature thymocytes by several events including specific activation of the T cell receptor CD3 complex. Mature T cells are usually resistant to these apoptic stimuli and respond to T cell receptor stimulation by cell proliferation and cytokine secretion. Abnormal induction of apoptosis in mature T cells, however, is also known.

Apoptosis in CD4+ T cells has also been observed in HIV-infected individuals, especially upon T cell receptor activation. It has been speculated that the complexing of the external glycoprotein gp120 of HIV with the CD4+ receptor may cause apoptosis even in noninfected cells. See *Science* vol. 260 May 28, 1993, 1269–1270.

In view of the foregoing, it would be a significant advance in the field of AIDS-related treatment if CD4+ lymphopenia could be addressed therapeutically. It would also be advantageous to effectively treat HIV-initiated apoptosis of CD4 + T cells. The present invention addresses these needs.

SUMMARY OF THE INVENTION

In one aspect of the present invention there is provided a method of treating CD4+ T cell lymphopenia in humans. The method includes administering an effective amount of an adenosine degrading agent to a human in need of such treatment to provide a significant increase in the CD4+ levels and therefore reduce or eliminate the lymphopenia.

In another aspect of the invention there is provided a method of reducing CD4+ T cell apoptosis in susceptible mammals. A still further aspect of this invention includes a method of increasing the therapeutic effect of reverse transcriptase inhibitor agents or anti-vital agents used in the treatment of mammals. These methods also include administering an effective amount of an adenosine degrading agent to the patient in need thereof in order to reduce the T cell apoptosis and/or increase the therapeutic effect of the antiviral agent in patients receiving the agents.

The invention also includes a new use of adenosine deaminase or other adenosine degrading substances for treatment of certain medical conditions in mammals. The new use includes administering an effective amount of the adenosine deaminase in combination with one or more reverse transcriptase inhibitor agents or anti-viral agents a patient in need of such treatment. In this aspect of the invention, the adenosine deaminase is a useful adjunct in the treatment of Acquired Immunodeficiency Disease (AIDS) by assisting in the metabolism of various anti-viral drugs into active metabolites. For example, it has been found that adenosine deaminase appears to metabolize agents such as dideoxyinosine, halogenated derivatives of dideoxypurines and dideoxyadenosine and its derivatives. Further, the adenosine deaminase metabolites of many deoxynucleoside analogs have anti-viral activity which, in some cases, is activity greater than that of the parent compound. Thus, the adenosine deaminase agents can be used in treatments as a facilitator which acts to assist in the release of active agents from prodrugs. In addition, the anti-viral activity of these types of agents can be completely abrogated in the presence of adenosine deaminase inhibitors. Consequently, administering the adenosine deaminase agents described herein can block or limit the abrogation of anti-viral activity of the concomitantly administered anti-viral agent.

The adenosine degrading agents useful in carrying out the methods described herein include enzymes obtained from suitable mammalian sources as well as those prepared using recombinant techniques. One particularly preferred adenosine degrading agent is bovine adenosine deaminase (ADA). Such agents are administered in amounts which are described as being "an effective amount". As will be described in more detail below, amounts which are sufficient to substantially reduce or eliminate the lymphopenia and/or T cell apoptosis generally range from about 5 IU/kg/week to about 50 IU/kg/week and preferably from about 10 IU/kg/week to about 30 IU/kg/week.

In particularly preferred aspects of the invention, the adenosine degrading agent is a bovine adenosine deaminase enzyme administered as a polyethylene glycol conjugate such as that available from Enzon, Inc. under the trademark ADAGEN® (PEG-ADEMASE, BOVINE).

For purposes of the present invention, "lymphopenia" shall be understood to mean T-cell levels of less than 200 cells/µl, as measured by fluorescence activated cell sorting (FACS).

The term "oppommistic infection" shall be understood to mean an infection which usually occurs only in patients whose resistance is compromised or lowered by an unrelated condition, disease or as a result of drug therapy.

As a result of the present invention, the artisan is provided with a useful alternative or supplement to currently available AIDS therapies. While the treatment methods of the present invention are not anti-vital treatments, they nonetheless cause increases in CD4+ T cell lymphocytes and substantially reduce CD4+ T cell apoptosis, especially when given in combination with an anti-viral agent such as AZT. Patients receiving effective amounts of the agents described herein will therefore be better able to combat opportunistic-infections and have an improved quality of life.

For a better understanding of the present invention, reference is made to the following description and its scope will be pointed out in the appended claims.

DETAILED DESCRIPTION OF THE INVENTION

In one preferred aspect of the invention, a method of treating CD4+ T cell lymphopenia in HIV-infected patients is provided. The method includes administering an effective amount of an adenosine degrading agent such as an adenosine enzyme to a human in need thereof, whereby the rate of decline of the CD4+ T cell counts in the human is substantially reduced or reversed. Since the progressive decline in the T cell count is the hallmark of AIDS caused by infection with HIV, the ability to arrest and/or prevent falls in the CD4+ cell count below about 200/µl; or even reverse such low cell counts, will reduce or eliminate the patient's susceptibility to opportunistic infections. In preferred aspects of this embodiment, the method includes maintaining CD4+ levels of at least about 200 cells/µl or raising CD4+ cell counts above that level by administering a sufficient amount of the adenosine degrading agents described herein to a patient in need of such treatment.

The amounts of adenosine degrading agent used in the methods of the present invention are generally described as amounts which effectively achieve the sought after therapeutic effect, i.e. reversing the lymphopenic condition or increasing the therapeutic effect of anti-vital agents which inhibit reverse transcriptase in mammals. The maximal dosage is the highest dosage which does not cause clinically important side effects. The lowest dosage contemplated is that which is still effective enough to achieve the results described above. Naturally the doses will vary somewhat depending upon the adenosine degrading enzyme or analog or isoenzyme used but the adenosine degrading agent will usually be administered in amounts ranging from about 5 IU/kg/week to about 50 IU/kg/week and preferably in amounts ranging from about 10 IU/kg/week to about 30 IU/kg/week. It will be understood that the doses are described as being based on the amount of adenosine deaminase (ADA) administered. Such doses are given for purposes of illustration and those of ordinary skill in the art will determine optimal dosing of the adenosine degrading agent (ADA or related compound) based on clinical experience. It is to be understood that the administration of adenosine degrading agent will also be dependent upon the individual patient. For example, while it is contemplated that the adenosine degrading agent will be administered on a chronic basis in an effort to combat the HIV effects, it will also be understood from the foregoing that episodic administration of the adenosine degrading agent on an as needed basis is also contemplated.

In one particularly preferred aspect of the invention, the adenosine degrading agent administered is bovine adenosine deaminase (ADA) covalently conjugated to polyethylene glycol strands which is available under the tradename ADAGEN®, (PEG-ADEMASE, bovine) a product of Enzon, Inc., (Piscataway, N.J.). This particular agent is administered in accordance with the methods of the present invention parenterally in pharmaceutically acceptable solutions in amounts ranging from 10 IU/kg/week to about 30 IU/kg/week based on the ADA. Intramuscular administration of the ADA conjugate is particularly preferred. The ADA-polyethylene glycol conjugates can also be prepared using the techniques described in U.S. Pat. No. 5,324,844, the disclosure of which is hereby incorporated by reference. The '844 patent describes, among other things, forming a substantially hydrolysis-resistant urethane bond between the epsilon amino groups of enzymes and a functionalized terminal group. The linkage by which the enzyme is joined to the polymer strand(s) can be any moiety known in the art which sufficiently unites the enzyme and polymer so that the conjugate may be administered in a pharmaceutically acceptable manner. In addition to the urethane linkage, amide linkages are also preferred. An example of amide-linked polymer enzymes is found in U.S. Pat. No. 5,349,001, the disclosure of which is incorporated by reference herein. The '001 patent describes, inter alia cyclic imide-activated polyalkylene oxides and conjugation thereof with therapeutic proteins and enzymes including adenosine deaminase.

ADAGEN is currently used to treat human patients with severe combined immunodeficiency disease (SCID) secondary to an inborn mutation inactivating the gene for adenosine deaminase. In this condition, ADA levels are essentially undetectable (less than 1% of normal levels; see Hirschhorn, *Pediatric Research* 33 (suppl.):535–541, 1993). ADA deficiency results in accumulation of adenosine metabolites, especially deoxyadenosine triphosphate, which inhibit DNA synthesis and thus cause death of T cells. ADAGEN treatment reverses SCID by reducing deoxyadenosine triphosphate levels. See Blaese and Culver, *Immunodeficiency Reviews* 3:329–249 (1992).

It has been surprisingly found that a separate and unexpected benefit is realized when adenosine degrading agents such as adenosine deaminase are administered to HIV-infected patients in order to treat or prevent CD4+ lymphopenia. It is believed that accumulation of adenosine metabolites, especially deoxyadenosine triphosphate, does not play a significant role in the lymphopenic condition and therefore administration of adenosine degrading agents could not have been predicted to successfully treat the lymphopenic condition.

The adenosine degrading agents which can be administered in accordance with the methods of the present invention can be prepared or obtained from a variety of sources, including recombinant or mammalian-extracted ADA. Although bovine adenosine deaminase is particularly preferred when it is included as part of a polyethylene glycol conjugate, it is to be understood that the methods described and claimed herein can also be carried out using gene therapy techniques. In this aspect of the invention, ADA or a similar adenosine degrading agent is administered using, for example, the procedures described by Blaese and Culver in *Immunodeficiency Reviews* 3:329–349 (1992) and the references cited therein. The disclosure of the aforementioned *Immunodeficiency Reviews* 3:329–349 (1992) is incorporated by reference herein.

Cultures are established from CD34+ hematopoietic progenitor cells isolated from the blood of an HIV-infected human patient. See Chelucci et al., *Blood* 85:1181–1187, 1995, the disclosure of which is incorporated by reference herein. A portion of the culture is treated by retrovital-mediated transduction with the LASN vector. The LASN vector contains the human adenosine deaminase gene. Treated CD34+ cells containing the transduced ADA gene are then reinfused into the patient. Alternatively, ADA can be obtained from mammalian sources such as bovine, ovine, human, etc. It is to be understood that other substances including pro-enzymes, fractions of enzymes, and catalytic antibodies can also be included in the present invention.

As used herein, the expression "adenosine degrading agents" means all suitable substances which demonstrate in vivo activity to reduce adenosine levels and treat CD4+ T cell lymphopenia and/or combat the HIV-mediated CD4+ T cell apoptosis. These substances are prepared by using techniques known to those of ordinary skill in the art such as tissue culture, extraction from plant or animal sources or by recombinant DNA methodologies. Transgenic sources of enzymes, pro-enzymes and fractions thereof are also contemplated. Such materials are obtained from transgenic animals, i.e. mice, pigs, cows, etc. wherein the enzyme is expressed in milk, blood, or tissues. The catalytic antibodies can be prepared using recombinant technologies. The method by which the enzymatic substance is prepared or obtained for the treatment methods and conjugates of the present invention is not limited to those described herein.

Substantially non-antigenic polymer substances can be included in the ADA conjugates. Within this group of substances are alpha-substituted polyalkylene oxide derivatives such as methoxypolyethylene glycols or other suitable alkyl substituted derivatives such as $C_1$-$C_4$ alkyl groups. It is preferred, however, that the non-antigenic material be a monomethyl-substituted PEG homopolymer. Alternative polymers such as other polyethylene glycol homopolymers, polypropylene glycol homopolymers, other alkyl-polyethylene oxides, his-polyethylene oxides and co-polymers or block co-polymers of poly(alkylene oxides) are also useful. In those aspects of the invention where PEG-based polymers are used, it is preferred that they have molecular weights of from about 1,000 to about 100,000. Molecular weights of about 2,000 to 40,000 are preferred and molecular weights of about 5,000 are especially preferred.

Alternative non-antigenic polymeric substances include materials such as dextran, polyvinyl pyrrolidones, polysaccharides, starches, polyvinyl alcohols, polyacryl amides or other similar non-immunogenic polymers. Those of ordinary skill in the art will realize that the foregoing is merely illustrative and not intended to restrict the type of non-antigenic polymeric substances suitable for use herein.

As stated above, a covalent modification of the adenosine degrading agent, enzyme or enzyme-like material with PEG or a related substantially related non-antigenic polymer is preferred to provide the hydrolysis-resistant conjugate. The covalent modification reaction of an adenosine degrading agent includes reacting a substance having the desired adenosine degrading activity with a substantially non-antigenic polymeric substance under conditions sufficient to effect conjugations while maintaining at least a portion of the ADA activity. See, for example U.S. Pat. Nos. 4,179,337 and 5,122,614, the disclosure of which are incorporated by reference herein. While the references incorporated herein describe epsilon amino group modifications of lysines found on the ADA, other conjugation methods are also contemplated. For example, modification of carboxylic acid groups and other reactive amino acid groups are also within the scope of the present invention. Covalent linkage by any atom between the adenosine degrading agent and polymer is possible. Moreover, non-covalent associations between polymer and adenosine degrading agent such as lipophilic or hydrophilic interactions are also contemplated.

Following the conjugation reaction, the desired product is recovered using known techniques and purified using column chromatography or similar apparatus if necessary. Depending upon the reaction conditions, the conjugates have from about 1 to about 25 polymeric strands attached to each molecule of the enzyme-like substance. By controlling the molar excess of the polymer reacted with the enzyme, for example, the artisan can tailor the number of polymeric strands attached. Conjugates containing from about 5 to about 20 polymeric strands are preferred while conjugates containing from about 10 to 18 polymeric strands are most preferred.

In alternative aspects of the invention, the adenosine degrading agent is administered in a liposome. A non-limiting example of such liposomes can be found in U.S. Pat. No. 4,534,899, the disclosure of which is incorporated herein by reference. Still further aspects of the invention include administering the adenosine degrading agent in the form of an oral dosage form which allows the agent to be bioavailable. It is to be understood from the foregoing that the delivery system selected or the means of administering the adenosine degrading agent to the patient is not to be construed narrowly and it is contemplated that any pharmaceutically acceptable delivery system can be used to carry out the inventive treatment methods.

Patients suffering from AIDS due to HIV infection have a severe lowering in the numbers of T lymphocytes circulating in their blood. This results in their resistance to infection being severely impaired. While Applicants are not bound by any particular theories, it is believed that the administration of ADA to CD4+ T lymphopenic or apoptoic patient in need thereof provides clinical benefits by reducing the level of circulating adenosine and thus reducing apoptosis of CD4 + T lymphocytes. Alternatively, ADA may act by blocking the binding of HIV to the CD4+ T lymphocytes by competitively blocking the gp120 binding coreceptor sites which are designated CD26 and it has been postulated that in order for the HIV to gain entry into the T cells, this coreceptor must also be available. In addition, ADA- based therapies may also have a direct effect on CD4+ cells. For example, ADAGEN is an FDA approved drug which has been shown to promote maturation of T lymphocytes. As a result, the benefits from the ADA-based treatment method include an increase in patient's personal sense of well being, decreases in the numbers of infections and a sustained increase in the numbers of circulating CD4 +T cells in their blood.

In yet a still further aspect of the invention, there is provided another method of treating HIV-infected humans. In particular, there is provided a method enhancing the therapeutic effect of antiviral agents in HIV-infected humans. This method, as described above, would appear every weekly This aspect includes administering an effective amount of an adenosine degrading agent as described above in combination with an effective amount of an antiviral agent. Suitable antiviral agents include without limitation, 3' azidothymadine (AZT, zidovudine), 2',3'-dideoxyinosine (ddI, didanosine), 2',3'-dideoxycytidine (DDC, zalcitabine) and the like and mixtures thereof. The exact amounts of such antiviral agents will be apparent to those of ordinary skill in the art based on clinical experience. Generally, however, it is contemplated that these agents be administered in FDA-approved amounts, such as those set forth in the *Physician's Desk Reference*, current addition. For purposes of the present invention, the term "in combination with" shall be understood to mean that the adenosine degrading agent is administered at not only the same time as the antiviral agent but also within a time which allows the combination of antiviral and adenosine degrading agent to have its synergistic effect. Thus, the adenosine degrading agent can be administered at the start of, during or substantially immediately after a course or antiviral agent(s). In this aspect of the invention, synergistic effects are observed.

In yet a still further aspect of the invention, there is provided a method of treating adenosine-induced T-cell toxicity in humans. The method includes administering an effective amount of an adenosine degrading agent to a patient in need thereof. This method of treatment is to be contrasted with the treatments used for SCID (described above) since it is not necessary that patients in need of the treatment described herein, to arrest adenosine induced toxicity, have the severely deficient ADA levels observed in patients presenting with SCID. The amounts of the adenosine degrading agent administered in this aspect of the invention will be in the same range as those described herein for the other treatments described.

EXAMPLES

The following examples serve to provide further appreciation of the invention but are not meant in any way to restrict the effective scope of the invention.

Example I

Modification of bovine adenosine deaminase with SC-PEG

In this example, bovine adenosine deaminase (ADA) obtained from Sigma Chemical Co. (St. Louis, Mo.) is conjugated with the activated poly(ethylene glycol)-N-succimimide carbonate (SC-PEG) described in U.S. Pat. No. 5,324,844. The PEG polymer has a molecular weight of about 5,000.

10 mg of ADA in 92 Mm NaOAc pH 5.8/10% glycerol/18% EtOH is dialyzed with 0.1 M sodium phosphate buffer solution, pH 7.0 using a Centricon-10 (a product of the Amicon Corporation of Beverly, Mass.). The final concentration of the ADA is ~0.5 mg/ml. Next, 100 mg of SC-PEG (10-fold excess by weight=120 molar excess) is added to the enzyme solution and the reaction mixture was stirred for 1 hr. at room temperature. The reaction is quenched by adding 0.1 M glycine. The unreacted PEG is removed by dialysis into a buffer solution having a pH of 6.5. The extent of modification is checked by SDS-gel.

Example II

In this example, the ability to use adenosine deaminase in the treatment of and/or prevent severe T cell lymphopenia in patients with HIV was demonstrated. ADAGEN® (PEG-ADEMASE.bovine) is a product of Enzon, Inc., (Piscataway, N.J.). The drug was administered to 17 patients enrolled in this study. Entry criteria into the study included a CD4+ T lymphocyte count of about 200 cells/µl or less and no past history of substance abuse. Patients remained under the care of their treating physician, and no alterations were made to other drug therapy. The patients were evaluated at baseline to determine their history, including documentation of the numbers of oppommistic infections, physical examination, and a baseline hematologic profile including T cell subsets.

The patients received parenteral (intramuscular) ADAGEN, 1500 IU intramuscularly once weekly for 12 weeks in combination with their current AZT or other anti-viral regimen. This data was compared to historical data used as a control Kahn et al. *NEMJ* 327,581 (1992) and Eron et al. *NEJM* 333, 1662 (1995), the contents of each are incorporated by reference herein. In Kahn et al., for example, the decline in efficacy over time for AZT is documented. Another study (Spruance, S. L. et al. *Annals of Internal Medicine* Vol. 120, No. 5, Mar. 1, 1994 pp 360–368) reported that HIV patients receiving zidovudine (AZT) experienced a chronic decrease in $CD4^+$ cells over the initial 12 week period of the study.

The patients receiving ADAGEN were monitored with T cell subset measurements. The results of the T cell subset measurements shown below indicate that the CD4+ T cell subset measurements for the patients receiving ADAGEN in combination with their current anti-viral therapy were either higher or did not decrease as much as would have been expected in view of the previous study.

| Patient | Initial CD4+ Count | Duration of Treatment (Weeks) | Final CD4+ Count | Change in CD4+ Count |
|---|---|---|---|---|
| 1. | 22 | 12 | 16 | −6 |
| 2. | 42 | 12 | 20 | −22 |
| 3. | 162 | 12 | 177 | +15 |
| 4. | 28 | 12 | 16 | −12 |
| 5. | 22 | 12 | 13 | −9 |
| 6. | 0 | 12 | 5 | +5 |
| 7. | 22 | 12 | 17 | −5 |
| 8. | 48 | 12 | 14 | −34 |
| 9. | 55 | 12 | 143 | +88 |
| 10. | 70 | 12 | 120 | +50 |
| 11. | 108 | 12 | 186 | +78 |
| 12. | 165 | 9 | 140 | −25 |
| 13. | 170 | 11 | 252 | +82 |
| 14. | 171 | 12 | 186 | +15 |
| 15. | 112 | 9 | 98 | −14 |
| 16. | 210 | 17 | 305 | +95 |
| 17. | 160 | 19 | 150 | −10 |

The Table in particular demonstrates that the chronic decline in $CD4^+$ cells known to occur in patients receiving anti-viral therapy with agents such as AZT can be significantly reduced or even reversed by administering adenosine deaminase in combination with the anti-viral agent. Indeed, the average CD4+ cell count improved an average of 17.1 in the patients treated with ADAGEN. The historical control dam indicates that an average decrease of about 23 to 25% in CD4+ cells would have been expected. An additional result observed was the fact that none of the patients in the study had an adverse reaction caused by the ADAGEN. The patients in the study also did not experience any opportunistic infections during the course of the study. The historical data suggested from about 6.7 to about 8.5% of the patients would have had at least one opportunistic infection during the course of the study. Most of the patients reported some improvement in well-being from being an on the treatment regimen. Finally, no deaths were observed in the ADAGEN treated patient group whereas the control data would suggest that from about 10-20% would have died during the course of the study.

Example III

In this example, ADA is administered by gene therapy methods following the procedures described in Blaese and Culver, *Immunodeficiency Reviews* 3:329-349 (1992) and the references cited therein.

Cultures are established from CD34+ cells isolated from the blood of an HIV-infected human patient by the methods of Chelucci et al., (*Blood* 85:1181-1187, 1995). The CD34+ cells may optionally be rendered resistant to HIV infection by transformation with an anti-HIV vector such as that of Buonocore et al., *PNAS* 90:2695-2699, 1993) or that of Marasco et al., (*PNAS* 90:7889-7893, 1993), the disclosures of which are incorporated by reference herein. A portion of the culture is then treated by retroviral-mediated transduction with the LASN vector described by Blaese and Culver, supra. The LASN vector contains the human adenosine deaminase gene. Treated T cells containing the transduced ADA gene are then reinfused into the patient. The patient exhibits increased levels of ADA resulting in increased levels of CD4+ T lymphocytes and decreased occurrence of opportunistic infections.

While there have been described what are presently believed to be the preferred embodiments of the present invention, those skilled in the art will realize that changes and modifications may be made thereto without departing from the spirit of the invention. It is intended to claim all such changes and modifications as fall within the true scope of the invention.

What is claimed is:

1. A method of treating CD4+ T cell lymphopenia in a human patient infected with a human immunodeficiency virus, comprising administering an effective amount of a suitable adenosine degrading agent.

2. The method of claim 1, wherein said adenosine degrading agent is an adenosine deaminase enzyme.

3. The method of claim 1, wherein said adenosine degrading agent is selected from the group consisting of bovine adenosine deaminase, human adenosine deaminase, and mixtures thereof.

4. The method of claim 2, wherein said adenosine deaminase enzyme is administered to said mammal in the form of a polyethylene glycol conjugate.

5. The method of claim 4, wherein said adenosine deaminase enzyme is derived from a bovine source.

6. The method of claim 5, wherein said effective amount of said adenosine deaminase is from about 1 to about 100 mg/kg/week.

7. The method of claim 6, wherein said effective amount of said adenosine deaminase is from about 5 to about 50 mg/kg/week.

8. The method of claim 7, wherein said effective amount of said adenosine deaminase is from about 10 to about 30 mg/kg/week.

9. A method of increasing CD4+ T lymphocytes counts in a human subject infected with a human immunodeficiency virus comprising administering an effective amount of a suitable adenosine degrading agent to a human subject in need thereof, said increase measured relative to CD4+ T cell counts in the same subject untreated by an adenosine degrading agent.

10. A method of preventing T cell apoptosis in a human subject infected with a human immunodeficiency virus, comprising administering an effective amount of a suitable adenosine degrading agent to a human subject in need thereof.

11. A method of enhancing the therapeutic effect of antiviral agents administered to a human subject infected by a human immunodeficiency virus, comprising administering a suitable adenosine degrading agent that is effective to stabilize or enhance CD4+ T cell counts relative to the CD4+ T cell counts in the same subject untreated by an adenosine degrading agent, said adenosine degrading agent being administered in an effective amount, said adenosine degrading agent being administered in combination with an effective amount of a anti-human immunodeficiency virus antiviral agent to a human subject in need thereof.

12. The method of claim 11, wherein said anti-viral agent is selected from the group consisting of AZT, zidovudine, didanosine, zalcitabine and mixtures thereof.

13. A method of enhancing the therapeutic effect of antiviral agents administered to a human subject infected by a human immunodeficiency virus, comprising administering an effective amount of a conjugate comprising a suitable adenosine degrading enzyme covalently linked to a substantially non-antigenic polymer, said conjugate administered in combination with an effective amount of an anti-human immunodeficiency virus antiviral agent, wherein said conjugate is administered in an amount effective to stabilize or enhance CD4+ T cell counts.

14. The method of claim 13 wherein said adenosine degrading enzyme is equivalent to an adenosine degrading enzyme derived from a bovine source.

15. The method of claim 13 wherein said antiviral agent is selected from the group consisting of AZT, zidovudine, didanosine, zalcitabine and mixtures thereof.

16. The method of claim 13, wherein said substantially non-antigenic polymer comprises a polyalkylene oxide.

17. The method of claim 16, wherein said polyalkylene oxide comprises polyethylene glycol.

18. The method of claim 9 wherein the CD4+ T lymphocytes counts are stabilized or increased to at least 200 cells/µl.

* * * * *